US005802743A

United States Patent [19]

Chien

[11] Patent Number: 5,802,743

[45] Date of Patent: Sep. 8, 1998

[54] STRUCTURE OF MASSAGING SLIPPER

[76] Inventor: Kuo-Ching Chien, No. 7, Lane 74, Kung-Wu Road, Lung-Tan, Taiwan

[21] Appl. No.: 935,779

[22] Filed: Sep. 23, 1997

[51] Int. Cl.$^{6}$ .............................. A61F 5/14

[52] U.S. Cl. .............................. 36/141; 36/11.5

[58] Field of Search .............................. 36/141, 136, 11.5, 36/28

[56] References Cited

U.S. PATENT DOCUMENTS

| | | | |
|---|---|---|---|
| 3,612,043 | 10/1971 | Inaki | 36/141 |
| 5,553,398 | 9/1996 | Schnewlin-Maier | 36/141 |
| 5,682,690 | 11/1997 | Chang | 36/141 |

*Primary Examiner*—M. D. Patterson

*Attorney, Agent, or Firm*—Bacon & Thomas

[57] ABSTRACT

A structure of massaging slipper, especially a structure of massaging slipper wherein a movable massaging ball is mounted for doing massage when it is worn on a foot, the massaging slipper is comprised of a slipper, an elastic gasket and a massaging ball, wherein the slipper is provided on its top surface with a round hole which receives therein by insertion a plunger on which the elastic gasket is placed, the massaging ball is placed on the elastic gasket and the plunger and is embedded in the round hole not to drop; the massaging ball is located exactly to be opposite to the middle of the sole of a foot, so that the foot of a person wearing the slipper can be massaged; the massaging ball can alternatively be taken to massage muscles of the body of the person, hence the slipper can have multiple functions, and thus is more practical.

1 Claim, 3 Drawing Sheets

STRUCTURE OF MASSAGING SLIPPER

BACKGROUND OF THE INVENTION

1. Field of the Invention

The present invention is related to a structure of massaging slipper, and especially to a structure of massaging slipper wherein a movable massaging ball is mounted for doing massage when it is worn on a foot, the massaging ball is used to massage the acupuncture points on the bottom of the foot to benefit health of a person, the massaging slipper is an excellent invention further in that it is portable and capable of being conveniently and easily used at any time and any place.

2. Description of the Prior Art

People wear shoes and sockets in a formal circumstance to express politeness and respect, and wear slippers for comfort and easiness outside of formal circumstances, slippers are essential daily necessities; there are various slippers in the markets, while slippers ordinarily are simple in design for wearing only, they do not have other function; some slippers are provided with small protrudings for massaging the bottoms of feet, if the small protrudings are too small or too soft, effect of massaging can not be achieved, and if they are too large or too hard, wearing of the slippers will be uncomfortable, this is surely not good, such kind of slippers with small protrudings are mainly made of plastic or rubber, plastic and rubber are harder material with inferior elasticity, a person wearing the slippers may feel pain of stabbing, and effect of massaging of the slippers is not good, therefore they are not poplularly used, the slippers can only be worn indoors, and actually do not have other function.

SUMMARY OF THE INVENTION

In view that slippers are so important in daily life of peple, they are long used every day, in order to elevate their value of use in increasing other functions when they are worn, the inventor of the present invention provides slippers, which are provided with movable balls to make massaging effect on feet to practically benefit health when they are worn, based on his professional experience of years in manufacturing and selling such kind of products and after continuous study and improving and repetitious experiments and tests.

The primary object of the present invention is to provide slippers with movable massaging balls to make massaging effect on feet to practically benefit health when they are worn.

Another object of the present invention is to provide slippers wherein the said movable massaging balls are located exactly at the middle of the sole of feet, so that the weight of a person wearing the slippers can concentrate on the massaging balls to increase effect of massaging.

The present invention will be apparent in its practical structure and way of using after reading the detailed description of the preferred embodiment thereof in reference to the accompanying drawings.

DETAILED DESCRIPTION OF THE PREFERRED EMBODIMENT

Figure 1:
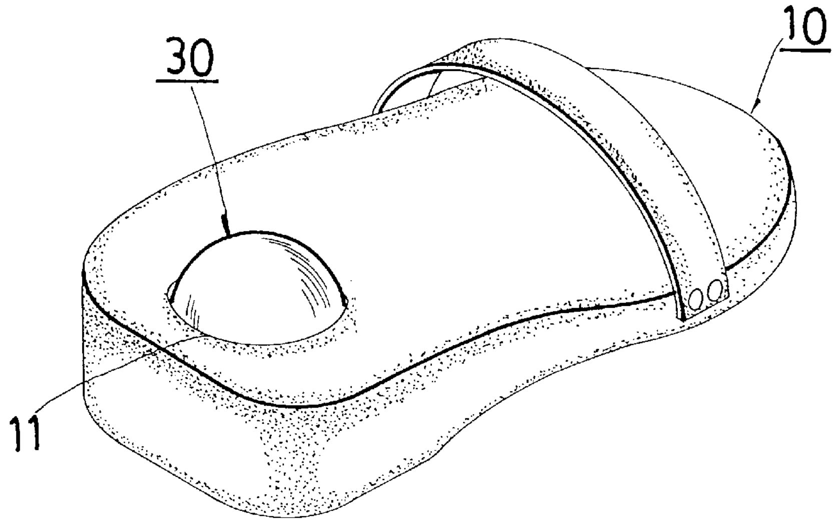
FIG. 1 is a perspective view of the present invention.
Figure 2:
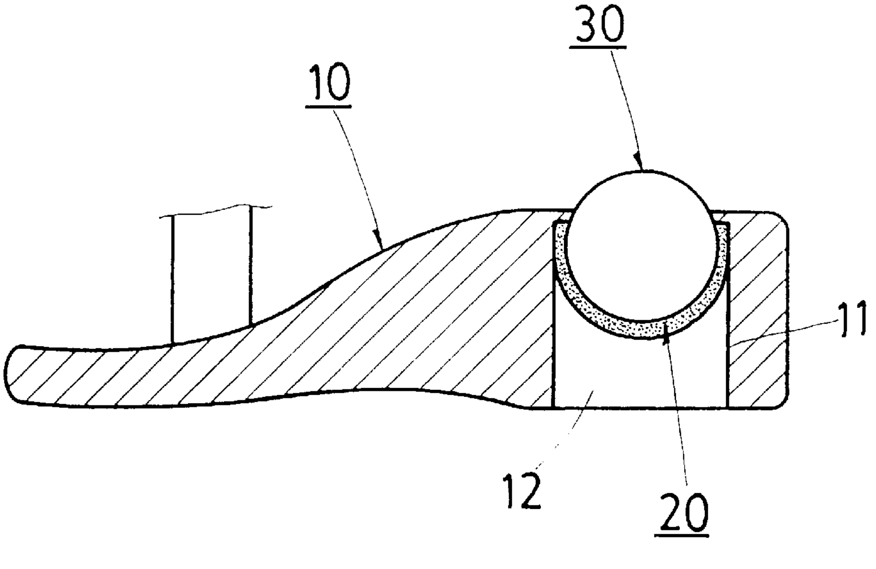
FIG. 2 is a sectional view of the structure of the present invention.
Figure 4:
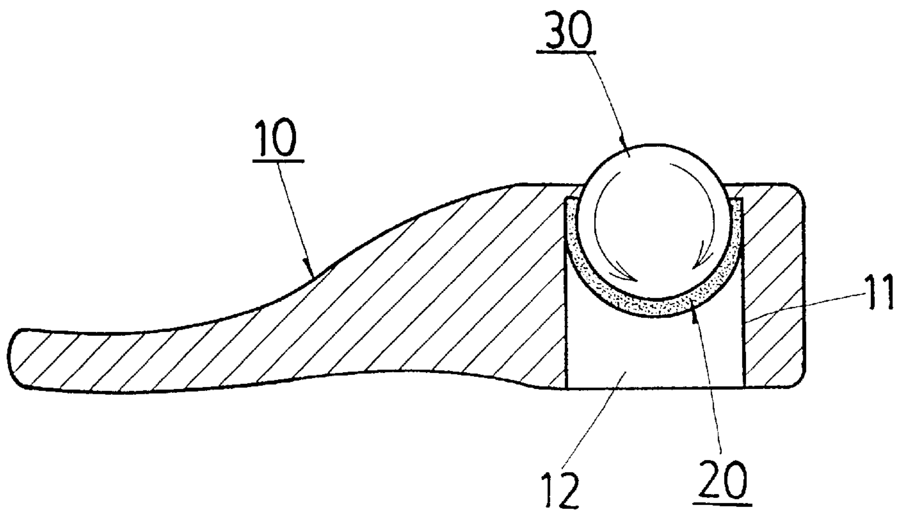
FIG. 4 is a schematic view showing the way of rolling of a movable massaging ball of the present invention.
Figure 5:
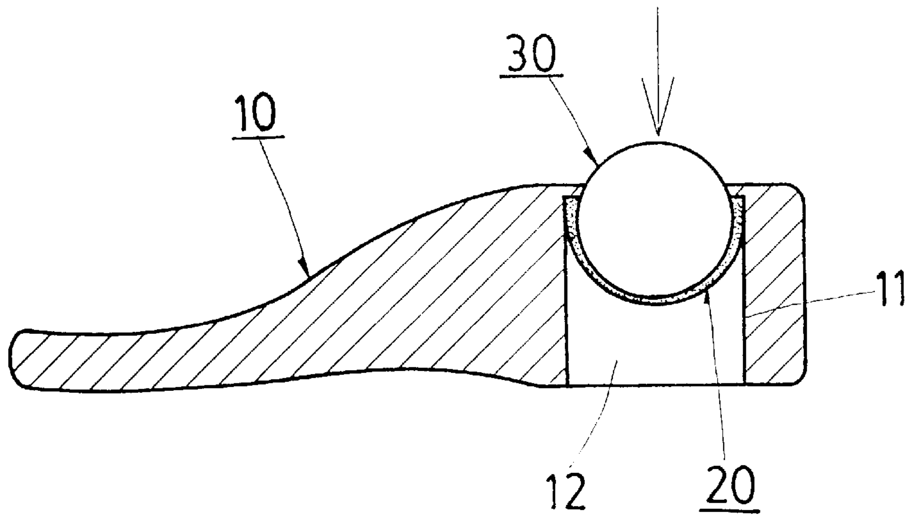
FIG. 5 is a schematic view showing the movable massaging ball of the present invention is pressed down.

Referring firstly to FIGS. 1 and 2, the structure of a massaging slipper of the present invention is comprised mainly of a slipper 10, an elastic gasket 20, a massaging ball 30, in which the slipper 10 is provided on the top surface thereof with a round hole 11 which receives therein by insertion a plunger 12 on which the said elastic gasket 20 is placed; the massaging ball 30 is placed on the elastic gasket 20 and the plunger 12 and are embedded in the round hole 11 not to drop, it is subjected to pushing force of the elastic gasket 20, and is provided with excellent effect of moving and rotating, when the massaging ball 30 is pushed and pressed, it is movable and rotatable in the round hole 11 by virtue of providing the elastic gasket 20 (such as are shown in FIGS. 2 and 4).

Figure 3:
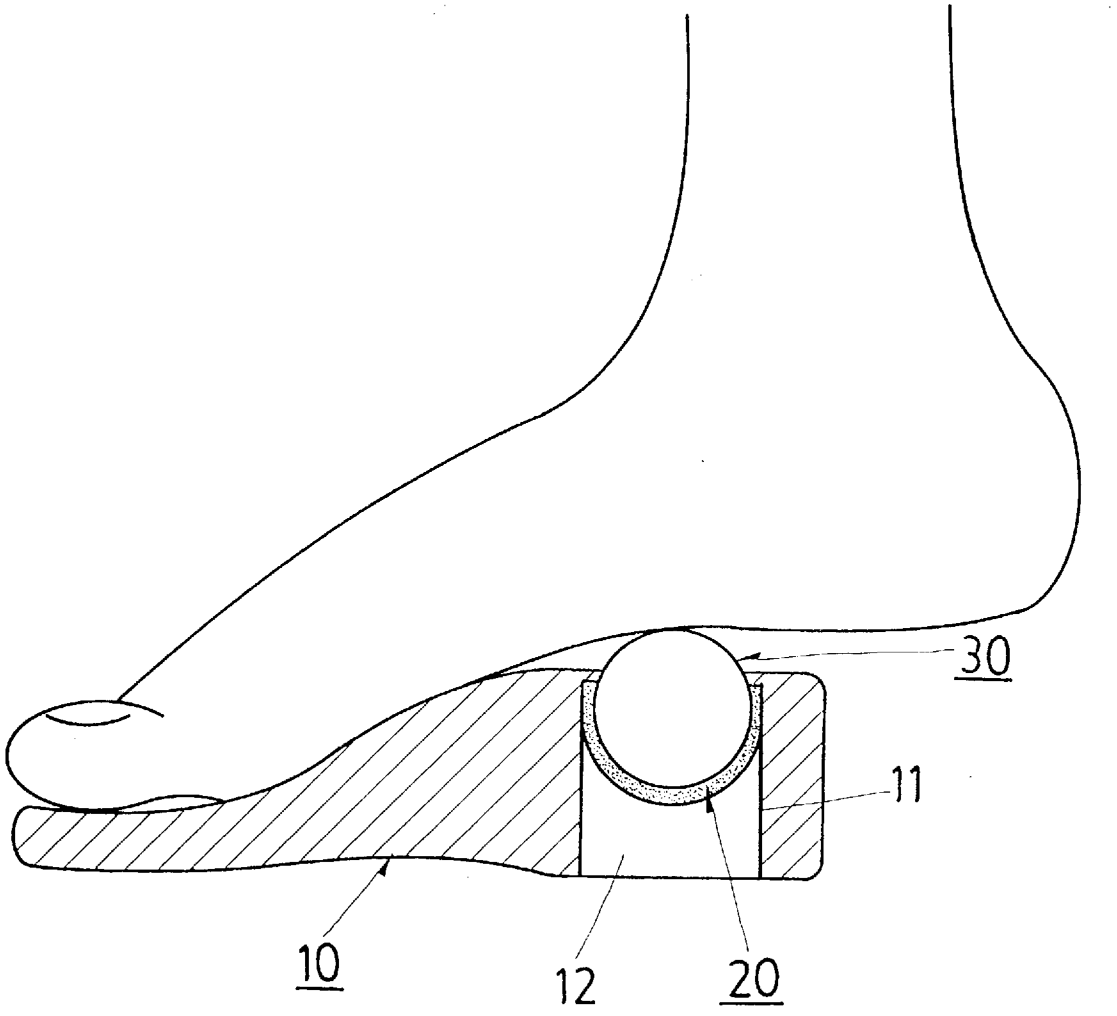
FIG. 3 is a schematic view showing the way of using of the present invention.

Referring then to FIGS. 3 and 4, the massaging ball 30 on the slipper 10 of the present invention is located exactly to be opposite to the middle of the sole of a foot, so that the weight of a person wearing the slipper 10 can concentrate on the massaging ball 30 to increase effect of massaging of the massaging ball 30 to the sole of the foot; alternatively, the slipper 10 can be placed flat on the ground, the person can step with the sole of his foot on the massaging ball 30 of the slipper 10, the foot can then twist or slide on the massaging ball 30 to sufficiently massage the sole of his foot without overly pressing the sole; or the slipper 10 can be taken with a hand to massage muscles of the body of the person with the massaging ball 30, therefore, the slipper 10 can have multiple massaging functions.

In conclusion, the slipper of the present invention is provided with a movable massaging ball, for doing massaging during wearing thereof, or the slipper can be taken with a hand to massage muscles of a person. Having thus described the structure of my invention with practicability and improveness, therefore.

What I claim as new and desire to be secured by Letters Patent of the United States is:

1. A structure of massaging slipper comprised of a slipper, an elastic gasket and a massaging ball, said structure is characterized in that:

said slipper is provided on the top surface thereof with a round hole which receives therein by insertion a plunger on which said elastic gasket is placed, said massaging ball is placed on said elastic gasket and plunger and is embedded in said round hole not to drop;

when said massaging ball is pressed by an external pushing force, it is movable and rotatable in said round hole by means of said elastic gasket provided at the bottom thereof and then is restorable to its original position.

* * * * *